US00PP35408P2

(12) United States Plant Patent
Alvarez Ramirez et al.

(10) Patent No.: US PP35,408 P2
(45) Date of Patent: Oct. 3, 2023

(54) PASSION FRUIT PLANT 'GRAND PASSION'

(50) Latin Name: ***Passiflora edulis* x *edulis flavicarpa***
Varietal Denomination: Grand Passion

(71) Applicants: Angel Gabriel Alvarez Ramirez, San Bartolome de la Torre (ES); Manuel Acosta Gaton, Huelva (ES)

(72) Inventors: Angel Gabriel Alvarez Ramirez, San Bartolome de la Torre (ES); Manuel Acosta Gaton, Huelva (ES)

( * ) Notice: Subject to any disclaimer, the term of this patent is extended or adjusted under 35 U.S.C. 154(b) by 0 days.

(21) Appl. No.: 17/960,873

(22) Filed: Oct. 6, 2022

(51) Int. Cl.
*A01H 5/08* (2018.01)
*A01H 6/00* (2018.01)

(52) U.S. Cl.
USPC ..... Plt./156

(58) Field of Classification Search
USPC ..... Plt./226, 156
CPC ..... A01H 6/00
See application file for complete search history.

(56) References Cited

PUBLICATIONS

CPVO hit to UPOV Plant Breeder's Right for a passionfruit vine denominated, 'Grand Passion', QZ PBR 2021/1874, application date Jul. 16, 2021.*

* cited by examiner

*Primary Examiner* — Karen M Redden

(57) ABSTRACT

A new and distinct cultivar of Passion Fruit plant named 'Grand Passion' is disclosed, characterized by its light satiny purple flower color, deep yellow fruit pulp color, and the balance between the acidity and brix presence in its pulp. The new variety is a *Passiflora*, normally used for outdoor ornamental purposes.

5 Drawing Sheets

Latin name of the genus and species: *Passiflora edulis* x *edulis flavicarpa.*

Variety denomination: 'Grand Passion'.

BACKGROUND OF THE INVENTION

Co-breeders Ángel Gabriel Álvarez Ramírez and Manuel Acosta Gascón have been developing a breeding program for new *Passiflora* varieties since 2016, carrying out crossings and/or pollinations of different varieties of the same species. It was in 2017, when they observed that in one of the vines of one of the crossings between an unnamed, unpatented variety of *Passiflora edulis* (female parent) and an unnamed, unpatented *Passiflora edulis flavicarpa* (male parent) the fruit had different characteristics not only to those of its parents but also to the other varieties of *Passiflora edulis* varieties, especially its size, color, flavour and scent. First asexual reproduction was conducted in San Bartolome de la Tone, Huelva, Spain in 2017. This vine was selected and grafted onto *Passiflora edulis flavicarpa*, undergoing evaluation for two seasons in 2018 and 2019, showing the same characteristics as the mother vine. These vines were obliterated by the "Filomena" storm in January 2021, except for one specimen which was planted and re-grafted that same year in 50 new specimens. During the 2020, 2021 and 2022 seasons, it was observed that the fruit from the selection maintained the distinctive characteristics of the selected parent.

SUMMARY OF THE INVENTION

The cultivar 'Grand Passion' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Grand Passion'. These characteristics in combination distinguish 'Grand Passion' as a new and distinct *Passiflora* cultivar:

1. Produces larger fruit than the seed parent, and smaller fruit than the pollen parent.
2. Light purple fruit skin color.
3. Medium green leaf color.
4. Deep yellow pulp color.

PARENT COMPARISONS

Plants of the new cultivar 'Grand Passion' are comparable to the seed parent, variety *Passiflora edulis*. The two *Passiflora* varieties are similar in most horticultural characteristics; however, the new variety 'Grand Passion' differs in the following:

1. Fruit of the new variety is larger than fruit of the seed parent.
2. Fruit color of the new variety is a lighter purple than fruit color of the seed parent.

Plants of the new cultivar 'Grand Passion' are comparable to the pollen parent *Passiflora edulis flavicarpa*. The two *Passiflora* varieties are similar in most horticultural characteristics; however, the new variety 'Grand Passion' differs in the following:

1. Fruit of the new variety is smaller than fruit of the pollen parent.
2. Fruit color of the new variety is light purple, while fruit color of the pollen parent is yellow.

COMMERCIAL COMPARISONS

Plants of the new cultivar 'Grand Passion' are comparable to the commercial variety *Passiflora* 'PANDORA', unpatented. The two *Passiflora varieties* are similar in most horticultural characteristics; however, the new variety 'Grand Passion' differs in the following:

1. Leaf color of the new variety is green, while the leaf color of this comparator is reddish-orange.
2. Flowers of the new variety are smaller than flowers of this comparator.
3. Seeds of this comparator are wider than seeds of the new variety.
4. Fruit skin color of the new variety is light purple, while fruit skin color of this comparator is reddish-purple.
5. First harvest of the new variety is earlier than the first harvest of this comparator.
6. The new variety is self-fertile, while this comparator is self-sterile.

Plants of the new cultivar 'Grand Passion' are comparable to the commercial variety *Passiflora* 'SILESIA', unpatented. The two *Passiflora* varieties are similar in most horticultural characteristics; however, the new variety 'Grand Passion' differs in the following:

1. Leaf blade of this comparator is longer and broader than the leaf blade of the new variety.
2. Leaf blade of this comparator has a deeper sinus and a weaker degree of blistering than the leaf blade of the new variety.
3. Petiole of the new variety is shorter than the petiole of this comparator.
4. Bract length of the new variety is longer than the bract length of this comparator.
4. Sepals of the new variety are longer and narrower than sepals of this comparator.
5. Petals of the new variety are longer than petals of this comparator.
6. Flowers of the new variety have a more deeply-colored spotted ring in the throat than flowers of this comparator.
7. Fruit lenticels of the new variety are less conspicuous than fruit lenticels of this comparator.
8. Seeds of the new variety are larger than seeds of this comparator.
9. Fruit pulp color of the new variety is orange-yellow, while fruit color of this comparator is orange.

BRIEF DESCRIPTION OF THE PHOTOGRAPHS

The accompanying photographic illustration shows typical specimens of vegetative growth of 4-year-old specimens of the new variety, in color as nearly true as it is reasonably possible to make in a color illustration of this character. Colors in the photograph may differ from the color values cited in the detailed botanical description above, which accurately describes the colors of the new Passion Fruit.

DETAILED BOTANICAL DESCRIPTION

Figure 1:
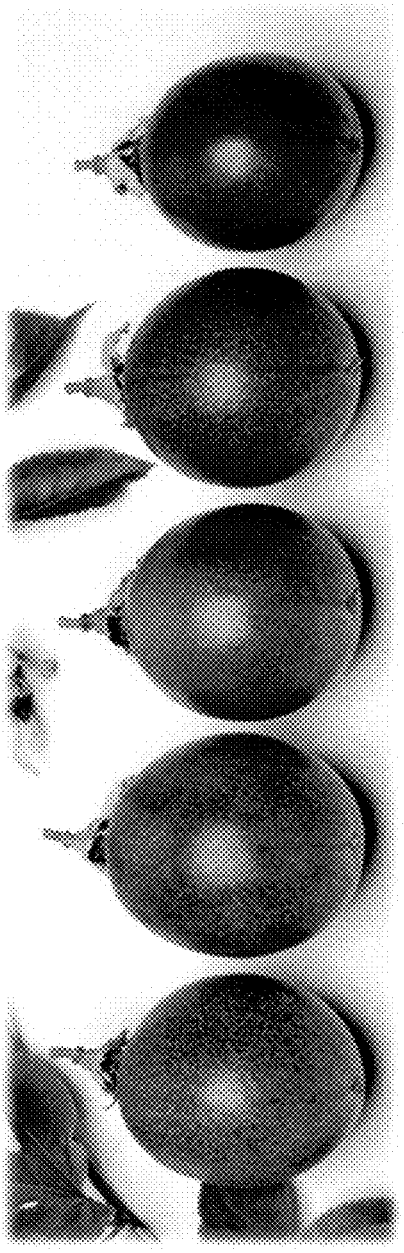
FIG. 1 illustrates in full color the ripening of the fruit, with the ripest fruit on the far right.
Figure 2:
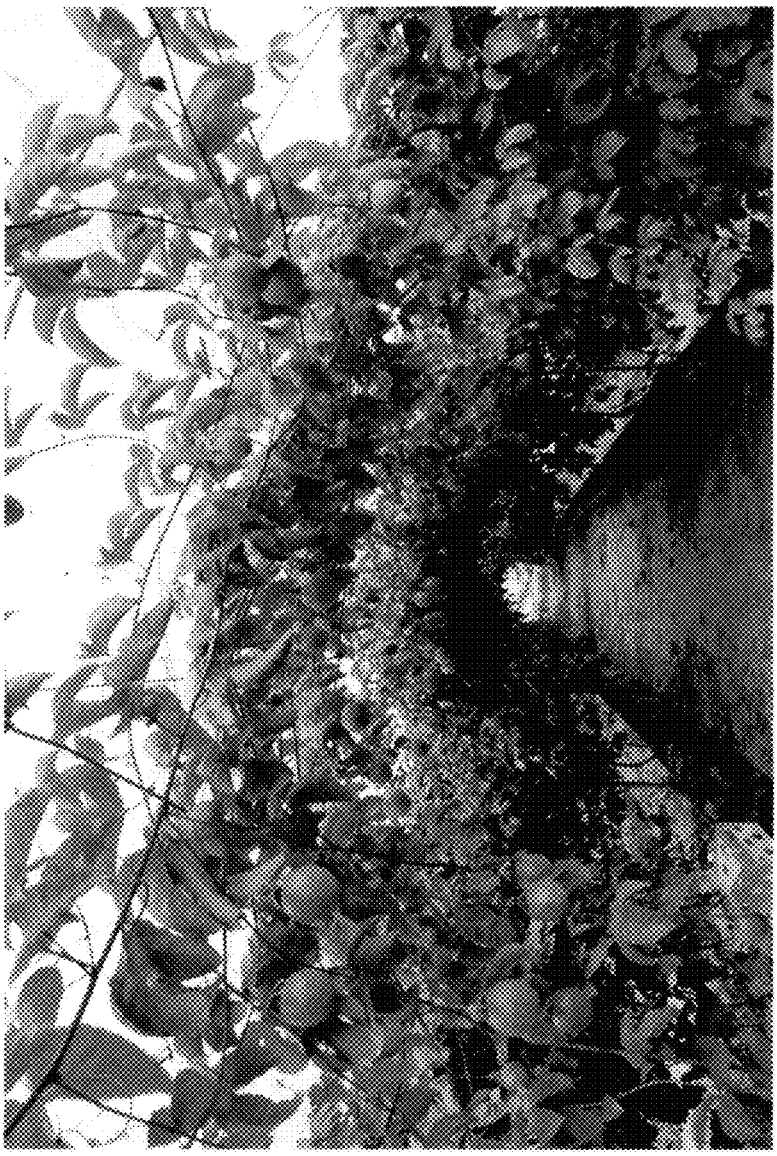
FIG. 2 illustrates in full color fruiting vines of 'Grand Passion' at approximately 2 to 3 years.
Figure 3:
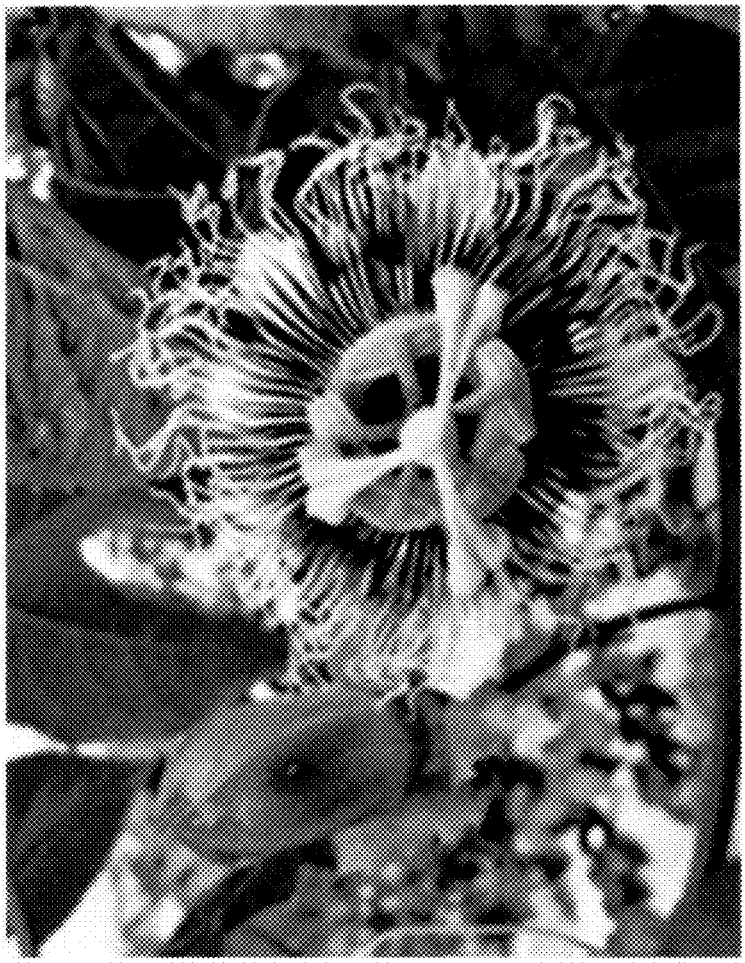
FIG. 3 illustrates in full color a flower of 'Grand Passion'.
Figure 4:
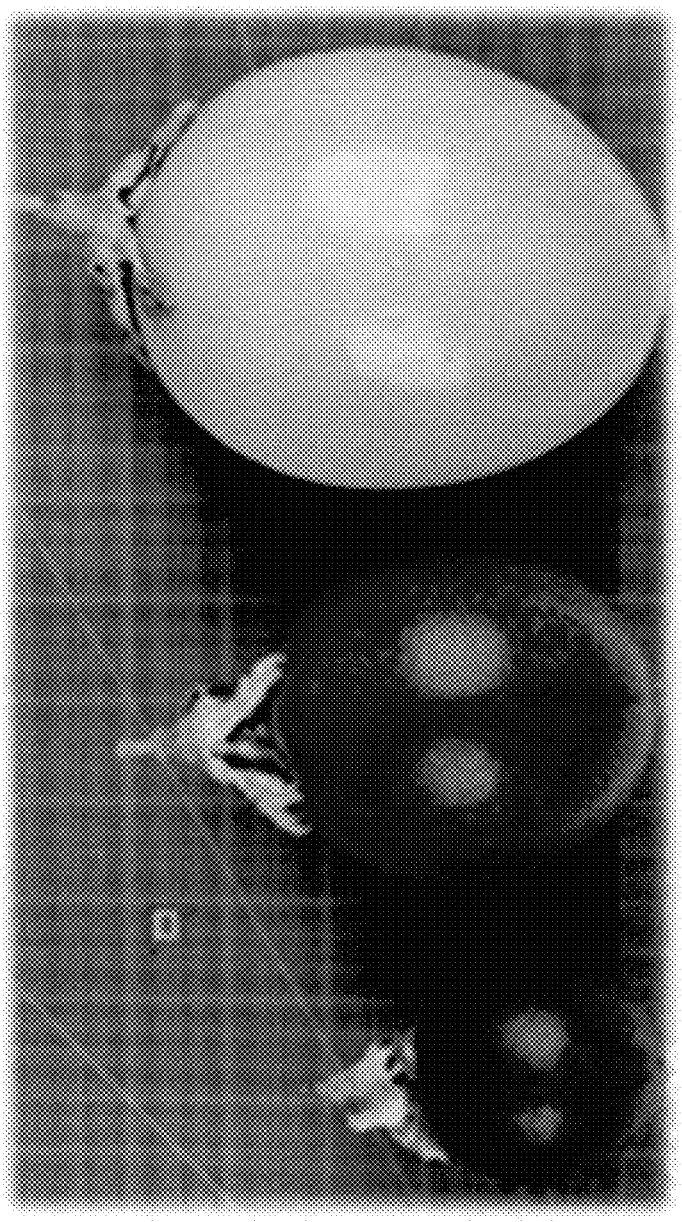
FIG. 4 illustrates in full color fruit of the seed parent on the left, 'Grand Passion' center and pollen parent on the right.
Figure 5:
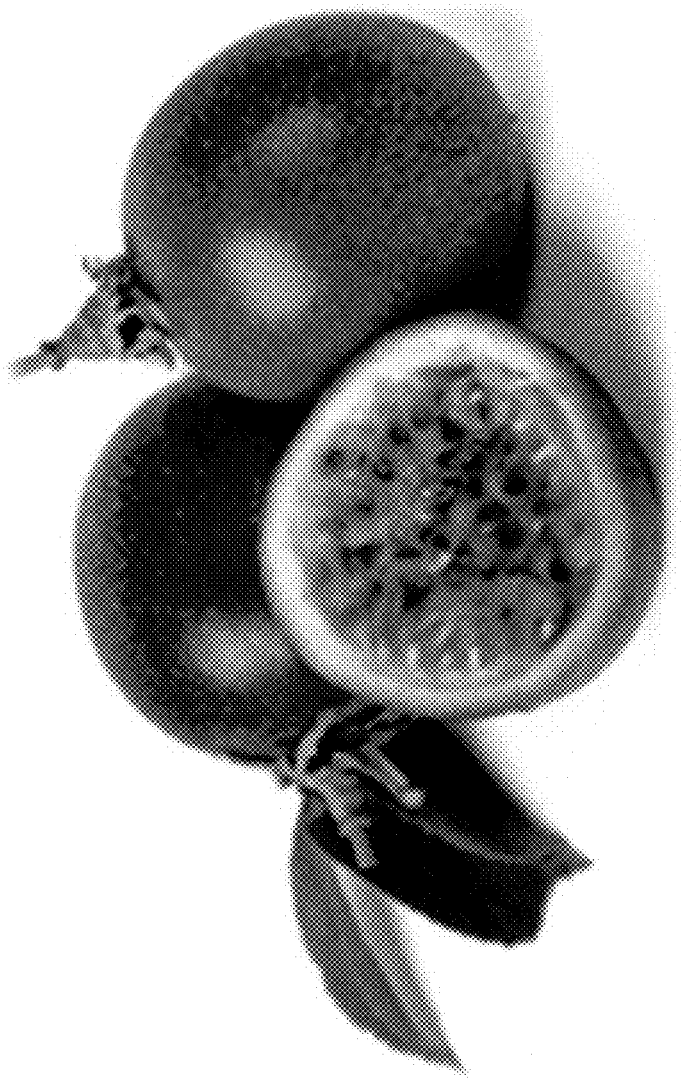
FIG. 5 illustrates in full color the fruit pulp of 'Grand Passion'.

For the following description of the new variety of *Passiflora*, the data has been observed and obtained under the climatic and environmental conditions existing in the evaluation fields located northern hemisphere in San Bartolomé de la Tone, Huelva, Spain, at approximately 128 meters above sea level, with a relative humidity of 30% in summer and 65% to 75% in winter. Minor variations in maturity dates and production may be due to agronomic management such as irrigation, fertilization, pruning and climate change. All main identification of colors is according to The ROYAL HORTICULTURAL SOCIETY (R.H.S.) Colour Chart 2015 edition.

Botanical classification: *Passiflora edulis* x *edulis flavicarpa* 'Grand Passion'.

PROPAGATION

Type of propagation typically used: Grafted stem cuttings.

PLANT

Age of plant described: 4 years.

Growth habit: Vertically ascending climbing vine.

Vigor: Very vigorous.

Plant spread: 500 cm.

Plant height: 300 cm.

Productivity: Very high, producing two harvests. Both harvests are uniform and produce 50% of its fruits in the winter harvest and the other 50% of its fruits during the summer harvest.

*Winter harvest.*—From the end of November to the end of January (February).

*Summer harvest.*—From mid-June to August.

Stem/trunk:

*Shape.*—Round and furrowed.

*Circumference.*—Young vine: 8 to 10 mm. Adult vine: 25 to 30 mm.

*Height.*—As it is a climbing vine, depends on the structure chosen by the grower. On the breeder's farm located in the northern hemisphere, a 3-meter-high trellis, under a tunnel hoop greenhouse with shade netting and a 5×2.5 planting frame between each vine, was used.

*Color.*—Young stems; RHS Green 142A. Mature stems: RHS Yellow-Green 147B with faint stripes near Purple 79C.

*Texture.*—Furrowed. Slightly rough. The skin of the stem has smooth grooves which are not very prominent. When young they are less pronounced than when mature

*Lenticels.*—Both the stem and the branches of the vine have vertical grooves 1 to 2 cm long, 1 to 2 mm width and long, light green when the stems or branches are young and brownish green when the stems or branches are mature.

*Internode length.*—Average 16 cm.

Branches:

*Length.*—500 cm.

*Texture.*—Slightly rough. The skin of the branches has grooves which become more pronounced with age. Young branches are slightly rough; grooves on adult branches are more prominent.

*Color.*—Young vine: RHS Yellow-Green 142A. Mature vine: RHS Yellow-Green 147B.

*Crotch angle.*—90 to 120°.

*Tendril*.—Axillary and originating from stem. Counterclockwise rotating (laevorotatory). Colored near Green 142C.

FOLIAGE

Leaf:
*Arrangement*.—3 deeply-lobed leaf.
*Length*.—Young vine: 20 cm. Mature vine: 30 cm.
*Width*.—Young vine: 20 cm. Mature vine: 30 cm.
*Shape of blade*.—Palmate composed of 3 lobes.
*Apex*.—Acute or apiculate.
*Base*.—Cordate.
*Margin*.—Serrated.
*Texture*.—Slightly rough.
*Color*.—Young foliage, face: RHS Yellow-Green 149A. Young foliage, blossom: RHS Yellow-Green 142A. Mature foliage, beam: RHS Green 135A. Mature foliage, underside: RHS Yellow-Green 149A.
*Venation*.—Pinnately reticulate. Color: Upper surface: Near Greyed-Orange 166B Lower surface: Near Green 142B.

Petiole:
*Length*.—Young leaf: 3 cm. Mature leaf: 7 cm.
*Width*.—Young leaf: 3 mm. Mature leaf: 5 mm.
*Color*.—RHS Yellow-Green 142A.
*Texture*.—Smooth, adaxial side is furrowed.
*Petiole glands*.—2, completely attached to the blade. Non-pubescent. Colored near Greyed-Orange N163A. About 4 mm in diameter.
*Nectar*.—Moderate to scant in quantity, translucent and viscous.
*Stipule*.—Paired, fleshy and rigid. Horn-shaped. 5 to 6 mm in diameter. Colored near Yellow-Green 142C.

FLOWER

Natural flowering season: April to August in summer; September to February in winter.
Flower size: Average 7 to 8 cm in diameter and 5 cm deep.
*Flower buds*.—Diameter: 5 to 6 cm. Shape: Bell-shaped.
Petals:
*Number*.—5.
*Apex*.—Acute.
*Base*.—Rounded.
*Length*.—3.5 cm.
*Width*.—1 cm.
*Color*.—Upper surface: RHS Green-White 157D. Lower surface: RHS Green-White 157D. Throat Color: White N155C and Yellow-Green 150D. Ring Color: Near Violet-Purple N92A. Outermost ring fades to Violet N88A and N88B.
Operculum: 6 to 11 mm thick. Colored near Yellow-Green 150D and Purple 79A.
Peduncle:
*Length*.—Average 7 cm.
*Color*.—RHS Yellow-Green 140D.
Sepals:
*Number*.—5.
*Color*.—Upper side: RHS Green-White 157D. Lower side: RHS Green 140D in center; Green-White 157D on edges. Sepal Awn: Present on underside of sepal, projecting at apex with flattened keel shape. Aristate apex. 3 to 6 mm long. Colored near Green-White 157D.
Bracts:
*Number*.—3.
*Shape*.—Elliptic, margin dentate.
*Color*.—Upper side: RHS Greyed-Orange N163A. Lower side: RHS Greyed-Orange N163A.

REPRODUCTIVE ORGANS

Stamens:
*Number*.—5.
*Filament color*.—RHS Yellow-Green 150, with Purple N186C speckles.
Style:
*Color*.—RHS Yellow-Green 150, with Purple N186C speckles.
Stigma:
*Shape*.—Capitate.
*Length*.—18 to 20 mm.
*Diameter*.—9 mm.
Ovary:
*Color*.—RHS White 157D.
*Shape*.—Ellipsoid.
*Texture*.—Glabrous.
*Length*.—1 cm.
*Diameter*.—6 to 7 mm.
Ovule:
*Color*.—RHS White 157D.
Anthers:
*Number*.—5.
Fragrance: Pleasant, acidic scent.
Pollen color: RHS Yellow 10D.
Flower filaments:
*Length*.—3.5 cm.
*Color*.—RHS Base near Violet-Blue N192A upper section near Green-White 157D
Androgynoiphore: 8 mm long, 3 mm in diameter. Colored near Green-White 157D.

FRUIT

Ripening:
*Winter*.—Mid-November.
*Summer*.—Mid-June.
Harvesting period:
*Winter*.—November to January.
*Summer*.—June to August.
Production:
*Young vine, winter*.—5 kg.
*Young vine, summer*.—20 kg.
*Adult vine, winter*.—20 kg.
*Adult vine, summer*.—20 kg.
Weight: Average 150 grams.
Shape: Ovoid (round or ovoid).
Size:
*Height*.—8.5 cm.
*Width*.—7.5 cm.
Pulp:
*Color*.—RHS Yellow-Orange 21A.
Skin:
*Outer skin color*.—RHS Purple N186D, lightly speckled near Yellow-Green 150D.
*Interior skin color*.—RHS White 155C.
*Fruit lenticels*.—Nearly inconspicuous. About 1 to 2 mm in diameter, round, colored near Green-White 157A.

Juice:

*Flavour*.—Mango/tangerine.

*Color*.—RHS Yellow-Orange 15A.

*Brix*.—18 to 20° in summer; 17 to 20° in winter.

Seeds:

*Shape*.—Ovoid.

*Seed external color*.—RHS Black 202A flushed Greyed-Purple N186A.

*Seed internal color*.—RHS Yellow-White N159D.

*Number of seeds per fruit*.—160 to 180.

*Size*.—Average 4 mm wide by 2 mm thick by 6 mm long.

OTHER CHARACTERISTICS

Disease resistance: Neither resistance nor susceptibility to diseases and pests of *Passiflora* observed to date.

Temperature range: Observed to tolerate a temperature range from 5° C. to 40° C. The fruit of the new variety has been found to display qualities suitable for handling and shipping combined with desirable dessert eating qualities, showing a life storage of 45 days at 6° C.

What is claimed is:

1. A new and distinct cultivar of *Passiflora* plant named 'Grand Passion' as herein illustrated and described.

* * * * *